(12) United States Patent
Heckerman (10) Patent No.: US 8,182,424 B2
(45) Date of Patent: May 22, 2012

(54) DIARY-FREE CALORIMETER

(75) Inventor: David E. Heckerman, Bellevue, WA (US)

(73) Assignee: Microsoft Corporation, Redmond, WA (US)

( * ) Notice: Subject to any disclaimer, the term of this patent is extended or adjusted under 35 U.S.C. 154(b) by 271 days.

(21) Appl. No.: 12/051,431

(22) Filed: Mar. 19, 2008

(65) Prior Publication Data

US 2009/0240113 A1 Sep. 24, 2009

(51) Int. Cl.
*A61B 5/00* (2006.01)
(52) U.S. Cl. .......................... 600/300; 600/587
(58) Field of Classification Search .......... 600/300–301, 600/587; 128/905, 920–921; 705/1–4; 482/4, 482/8–9
See application file for complete search history.

(56) References Cited

U.S. PATENT DOCUMENTS

| | | | | |
|---|---|---|---|---|
| 5,954,640 | A * | 9/1999 | Szabo | 600/300 |
| 6,478,736 | B1 * | 11/2002 | Mault | 600/300 |
| 6,513,532 | B2 * | 2/2003 | Mault et al. | 128/921 |
| 7,258,666 | B2 | 8/2007 | Brown | |
| 7,287,031 | B1 | 10/2007 | Karpf et al. | |
| 2004/0152957 | A1 * | 8/2004 | Stivoric et al. | 600/300 |
| 2006/0190295 | A1 | 8/2006 | Merkin | |
| 2007/0043535 | A1 | 2/2007 | Belden | |
| 2007/0061167 | A1 | 3/2007 | Brown | |
| 2007/0150311 | A1 | 6/2007 | Lazerus | |
| 2007/0167688 | A1 | 7/2007 | Ross et al. | |
| 2007/0198295 | A1 | 8/2007 | Duckert et al. | |
| 2007/0214007 | A1 | 9/2007 | Hackner | |

OTHER PUBLICATIONS

El Camino Hospital, "Improving Patient Care with Enterprise Systems Technology", 2005 Computerworld Honors Case Study,retreived at <<http://www.cwhonors.org/laureates/medicine/20055355.pdf>>, Apr. 2005, 5 pages.
Quadramed, "Care Management—Quadramed", retrieved on Oct. 25, 2007 at <<http://www.quadramed.com/care_management/>>, 11 pages.
"The Credit Valley Hospital", retrieved on Oct. 25, 2007 at <<http://www.microsoft.com/canada/casestudies/cvhospital.mspx>>, 2 pages.

* cited by examiner

*Primary Examiner* — Henry M Johnson, III
*Assistant Examiner* — Kai Rajan
(74) *Attorney, Agent, or Firm* — Lee & Hayes, PLLC (57) ABSTRACT

An indirect calorimeter estimates nutritional caloric intake by periodically monitoring weight and sensing physical exercise (i.e., physiological data and/or motion data related to physical exertion), which can then be used in a calorimetry model derived from regression analysis of a population (e.g., linear regression, feed-forward neural network, Gaussian process, boosted regression tree, etc.). A strap-on user device for tracking exercise can detect one or more of heart rate, body temperature, skin resistance, motion/acceleration sensing (e.g., pedometer, accelerometer), velocity sensing (e.g., global positioning system (GPS)), and an intelligent, integrated exercise machine (e.g., treadmill, exercise bike, etc.). To gain further fidelity, the user can fine-tune the estimate by undergoing a journal-based routine for a relatively short period of time or clinical calorimetry measurement (e.g., respiratory calorimeter), thereby providing a baseline for resting or exercising metabolic rate.

20 Claims, 6 Drawing Sheets

DIARY-FREE CALORIMETER

BACKGROUND

The present innovation pertains to determining nutritional caloric intake, and in particular to an approach that indirectly determines caloric intake usable outside of a clinical setting.

Significant development and investment has been made in accurately determining the calories in each kind of food. Examples of such technology include reaction calorimeters (e.g., bomb calorimeter), constant-pressure calorimeter, differential scanning calorimeter, isothermal titration calorimeter, X-ray microcalorimeter, heat-loss calorimeter, and high-energy particle calorimeter. References thus abound for providing nutritional content of food both in bulk and packaged for sale.

Leveraging such knowledge, many who seek to lose weight have had to maintain written journals of all foods eaten in order to gain awareness of their caloric intake. Thereby, limits on the total calorie and the types of calorie (e.g., fat, starch, protein, etc.) can be imposed. Although some have the discipline to objectively and consistently keep such journals, most find this technique too difficult.

A modest improvement has been realized with portable devices (e.g., personal digital assistants, digital notepads, etc.) that can record the journal information. Even with some assistance for calculating and tracking food intake, such devices still rely upon the user to remember to input the data and to be accurate about the quantities consumes. It has even been further proposed to have a portable photographic system that visually records images of the food consumed in order to keep better records. However, each of these approaches and devices suffer when the user is a social setting that is not conducive to recording such information (e.g., at a party, midnight snacking, etc.)

Even in clinical settings (e.g., hospitals, premier sports training programs, etc.) that have greater accountability over what food is served, often indirect calorimetry techniques are used. Presumably, diet journals would be nearly as cumbersome even in such environments. Typically, indirect calorimeters measure respiration flow rate and the fraction of the oxygen that is converted into carbon dioxide. These can be used to determine resting metabolic rate (RMR) or even metabolic efficiency during certain carefully orchestrated exercises (e.g., treadmill). Generally, such clinical respiration-based indirect calorimeters are not practical or desirable for everyday use.

SUMMARY

The following presents a simplified summary of the innovation in order to provide a basic understanding of some aspects described herein. This summary is not an extensive overview of the claimed subject matter. It is intended to neither identify key or critical elements of the claimed subject matter nor delineate the scope of the subject innovation. Its sole purpose is to present some concepts of the claimed subject matter in a simplified form as a prelude to the more detailed description that is presented later.

The subject innovation relates to systems and/or methods that provide a calorie intake estimate based upon monitoring exercise and weight changes. A model generated by regression analysis of a control population can be referenced to estimate this result. Thereby, the inconvenience and inaccuracy of monitoring calorie intake by calorie journals can be avoided. With awareness of the amount of exercise actually performed and the amount of calories consumed, the user can better gauge a behavior change to lose weight (i.e., exercise more or eat less).

In accordance with one aspect of the subject innovation, a method is provided for determining nutritional caloric intake. A portable sensor is worn for detecting a parameter associated with physical exercise over a measurement period. A current weight measurement of a user is compared with a stored prior weight measurement at the beginning of the measurement period. A model for caloric intake is accessed for estimating total caloric intake based upon the detected parameter, the prior weight, the current weight, and the caloric intake model and the caloric intake model.

In another aspect, an apparatus is provided for determining nutritional caloric intake. A portable sensor is worn by a user for detecting a parameter associated with physical exercise over a measurement period. A memory contains a stored prior weight measurement at the beginning of the measurement period and data from the portable sensor. A processor compares a current weight measurement of the user with the stored prior weight measurement, accesses a model for caloric intake, and estimates total caloric intake based upon the detected parameter, the prior weight, the current weight, and the caloric intake model.

In an additional aspect, a method is provided for determining nutritional caloric intake. A first portable sensor is worn for detecting a physiological parameter associated with physical exercise over a measurement period. A second portable sensor is worn for detecting a motion parameter associated with physical exercise over the measurement period. A current weight measurement of a user is compared with a stored prior weight measurement at the beginning of the measurement period. A model is accessed for caloric intake trained by performing regression analysis on caloric intake and weight changes for a control population. Total caloric intake is estimated based upon the detected physiological and motion parameters and the caloric intake model.

The following description and the annexed drawings set forth in detail certain illustrative aspects of the claimed subject matter. These aspects are indicative, however, of but a few of the various ways in which the principles of the innovation may be employed and the claimed subject matter is intended to include all such aspects and their equivalents. Other advantages and novel features of the claimed subject matter will become apparent from the following detailed description of the innovation when considered in conjunction with the drawings.

DETAILED DESCRIPTION

An indirect calorimeter estimates nutritional caloric intake by periodically monitoring weight and sensing physical exercise (i.e., physiological data and/or motion data related to physical exertion), which can then be used in a calorimetry model derived from regression analysis of a population (e.g., linear regression, feed-forward neural network, Gaussian process, boosted regression tree, etc.). A strap-on user device for tracking exercise can detect one or more of heart rate, body temperature, skin resistance, motion/acceleration sensing (e.g., pedometer, accelerometer), velocity sensing (e.g., global positioning system (GPS)), and an intelligent, integrated exercise machine (e.g., treadmill, exercise bike, etc.). To gain further fidelity, the user can fine-tune the estimate by undergoing a journal-based routine for a relatively short period of time or clinical calorimetry measurement (e.g., respiratory calorimeter), thereby providing a baseline for resting or exercising metabolic rate.

The claimed subject matter is described with reference to the drawings, wherein like reference numerals are used to refer to like elements throughout. In the following description, for purposes of explanation, numerous specific details are set forth in order to provide a thorough understanding of the subject innovation. It may be evident, however, that the claimed subject matter may be practiced without these specific details. In other instances, well-known structures and devices are shown in block diagram form in order to facilitate describing the subject innovation.

As utilized herein, terms "component," "system," "interface," "store," "device," "network," "cloud," and the like are intended to refer to a computer-related entity, either hardware, software (e.g., in execution), and/or firmware. For example, a component can be a process running on a processor, a processor, an object, an executable, a program, a function, a library, a subroutine, and/or a computer or a combination of software and hardware. By way of illustration, both an application running on a server and the server can be a component. One or more components can reside within a process and a component can be localized on one computer and/or distributed between two or more computers.

Furthermore, the claimed subject matter may be implemented as a method, apparatus, or article of manufacture using standard programming and/or engineering techniques to produce software, firmware, hardware, or any combination thereof to control a computer to implement the disclosed subject matter. The term "article of manufacture" as used herein is intended to encompass a computer program accessible from any computer-readable device, carrier, or media. For example, computer readable media can include but are not limited to magnetic storage devices (e.g., hard disk, floppy disk, magnetic strips . . . ), optical disks (e.g., compact disk (CD), digital versatile disk (DVD). . . ), smart cards, and flash memory devices (e.g., card, stick, key drive . . . ). Additionally it should be appreciated that a carrier wave can be employed to carry computer-readable electronic data such as those used in transmitting and receiving electronic mail or in accessing a network such as the Internet or a local area network (LAN). Specifically, the subject innovation can be utilized with a variety of hardware configurations such as, but not limited to disability assisted input/output facilities, voice enabled input/output, tactile (e.g., Braille, etc.) keyboard, etc. Of course, those skilled in the art will recognize many modifications may be made to this configuration without departing from the scope or spirit of the claimed subject matter. Moreover, the word "exemplary" is used herein to mean serving as an example, instance, or illustration. Any aspect or design described herein as "exemplary" is not necessarily to be construed as preferred or advantageous over other aspects or designs.

Figure 1:
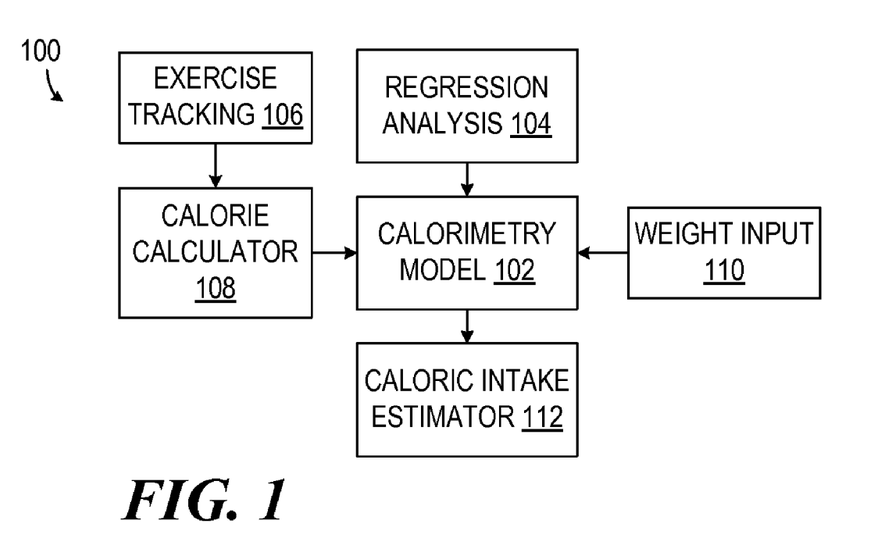
FIG. 1 illustrates a block diagram an apparatus for deducing calorie intake based upon a calorimetry model trained by regression analysis, exercise monitoring and weight inputs.

Now turning to the figures, FIG. 1 illustrates an apparatus 100 for deducing calorie intake based upon a calorimetry model 102 trained by regression analysis 104. Values for estimated nutritional caloric intake are derived from the model 102 for resting metabolic rate (RMR). This value is adjusted by tracking exercise data 106 that is used in a calorie calculator 108, thereby determining calories consumed by exercise. With total baseline calories calculated, periodically receiving a weight input 110 can then be used with the model to determine excess or deficit calories from the baseline that would have caused any upward or downward change respectively in weight. These results are combined for reporting to the user in a caloric intake estimator 112.

Figure 2:
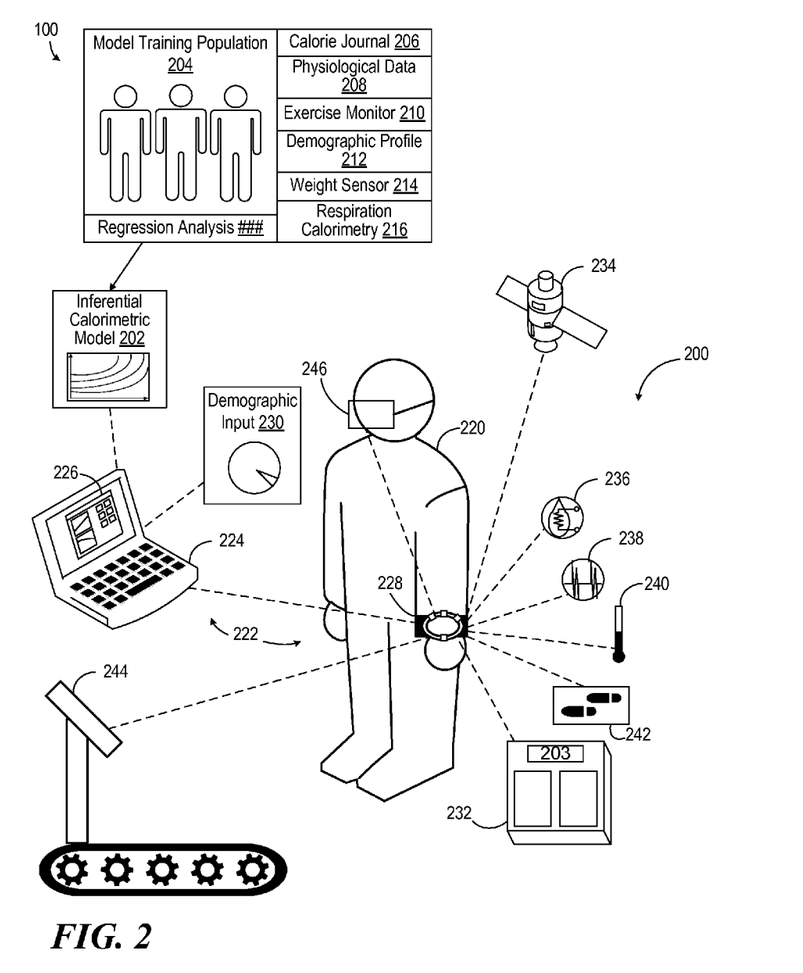
FIG. 2 illustrates a block diagram of a system for deducing calorie intake based upon a calorimetry model trained by regression analysis, exercise monitoring and weight inputs.

In FIG. 2, a system 200 is provided for deducing calorie intake based upon a calorimetry model 202, which is created by monitoring a population 204 used to train the model. While tracking the food intake of each member of this population 204, the other variables to be used in an uncontrolled setting are also monitored. For example, caloric intake can be determined by a calorie journal 206. Calories expended by exercise by the model training population 204 can be determined by one or more of physiological sensing 208 (e.g., pulse rate, body temperature, skin resistance, respiration rate, etc.) and exercise monitor data 210 (e.g., treadmill, exercise bike, etc., pedometer, GPS, etc.). The population 204 can be further differentiated based on certain demographic profiles 212 (e.g., sex, age, height, body type such as body mass index (BMI), etc.). A weight sensor 214 periodically obtains the weight for each individual. To further refine the model or to validate against other studies, an indirect respiration calorimetry 216 can be performed for either resting metabolic rate or exercising metabolic rate.

A user 220 can utilize the calorimetric model 202 on a calorimetric platform 222, which can be provided on various kinds of devices, or a plurality of interacting devices. In the illustrative depiction, a general purpose computer, depicted as a laptop 224, executes an application 226 that synchronizes with a portable device 228 that is strapped onto an arm of the user 220 to detect physiological data used to determine an amount of exercise. The combination thus allows additional user interface options and communication of a laptop 224 with the ease of portability of a small portable device 228, such as a Smart Personal Object Technology (SPOT) watch. Alternatively or in addition, the portable device 226 could be used without a laptop 222. As a further alternative, raw physiological or motion data detected by a portable sensor could be periodically downloaded to a device that is not worn (e.g., the laptop 222) for processing and interaction.

The user 220 inputs demographic data 230 into the calorimetric platform 222 (e.g., sex, age, BMI, etc.). Periodically, the user 220 can manually input weight information or a weight scale 232 can wirelessly communicate a weight. The calorimetric platform 222 can included integrated sensors or be in communication with various sensors. For example, motion and location can be enhanced by picking global positioning signals from GPS satellites 234. The calorimetric platform 222 can leverage physiological data from a skin resistance sensor 236, a cardiopulmonary rate sensor (e.g., pulse, respiration rate, etc.) 238, body temperature sensor 240, and a motion sensor (e.g., pedometer, accelerometer)

242. Similar data can be separately obtained and received from exercise equipment, depicted as a treadmill 244. Refinement of estimates can be obtained by interfacing with a respiratory calorimeter 246.

Figure 3:
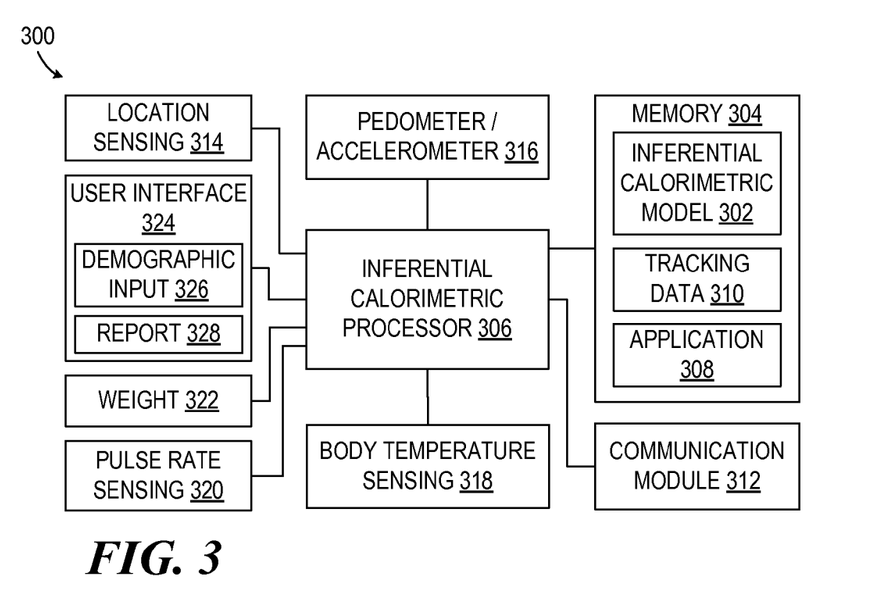
FIG. 3 illustrates a user device for deducing calorie intake based upon a calorimetry model trained by regression analysis, exercise monitoring and weight inputs.

FIG. 3 illustrates a device 300 worn by a user for deducing calorie intake based upon a calorimetry model 302 trained by regression analysis and contained in memory 304. An inferential calorimetric processor 306 accesses an application 308 in memory 304 and executes the application 308 to generate tracking data 310 stored in memory 304. This tracking data 310 can be received from distributed components or communicated for further processing via a communication module 312 (e.g., BLUE TOOTH, SPOT, short message service (SMS), etc.). An amount of exercise is determined by location sensing component 314, which can include velocity data. Alternatively or in addition, motion sensing can be determined from a pedometer/accelerometer 316. Alternatively or in addition, body temperature sensing 318 can enhance determination of metabolic rate. Physiological data such as cardiopulmonary indicators (e.g., pulse rate, heart rate, breathing rate, air flow rate, etc.) can be picked up by a sensor, depicted as a pulse rate sensor 320. A weight tracking component 322 can receive a weight data signal or store a value made upon a user interface 324. A higher fidelity estimate from the model 302 can be achieved by setting a demographic input 326 in the user interface 324. The tracking data or calculations made from them can be presented as reports 328 on the user interface 324.

Figure 4:
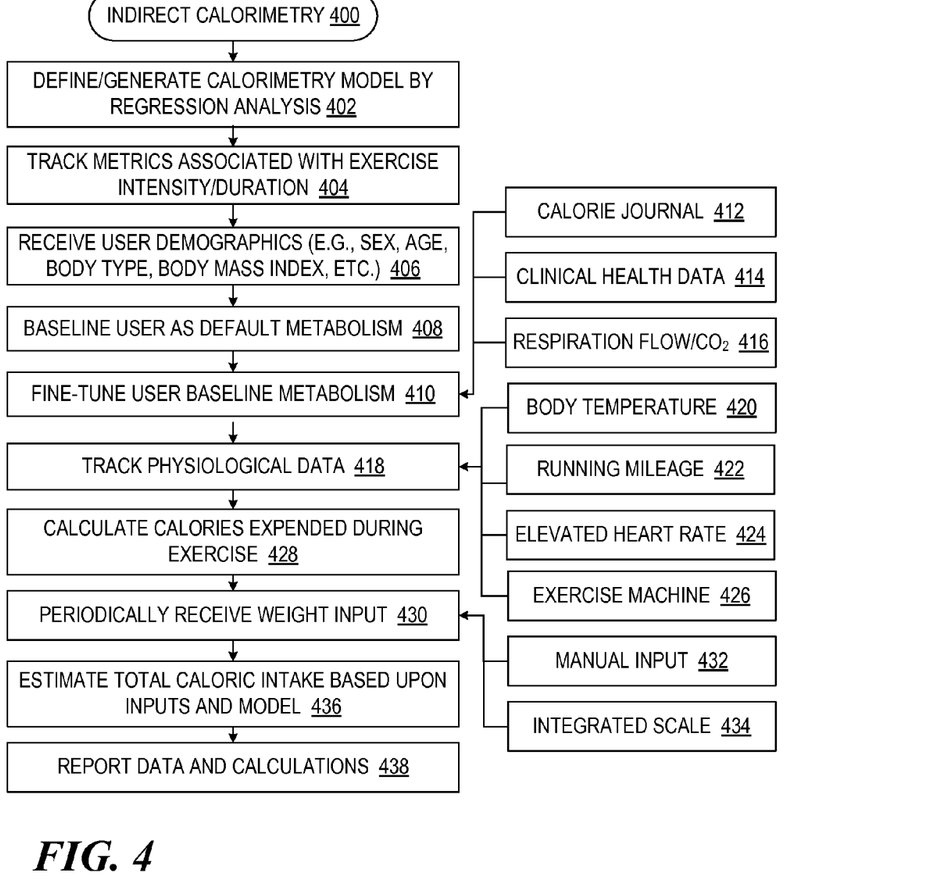
FIG. 4 illustrates a methodology for indirect calorimetry by periodically monitoring weight and exercise monitoring as inputs to a calorimetry model trained by regression analysis.

FIG. 4 illustrates methodologies and/or flow diagrams in accordance with the claimed subject matter. For simplicity of explanation, the methodologies are depicted and described as a series of acts. It is to be understood and appreciated that the subject innovation is not limited by the acts illustrated and/or by the order of acts. For example acts can occur in various orders and/or concurrently, and with other acts not presented and described herein. Furthermore, not all illustrated acts may be required to implement the methodologies in accordance with the claimed subject matter. In addition, those skilled in the art will understand and appreciate that the methodologies could alternatively be represented as a series of interrelated states via a state diagram or events. Additionally, it should be further appreciated that the methodologies disclosed hereinafter and throughout this specification are capable of being stored on an article of manufacture to facilitate transporting and transferring such methodologies to computers. The term article of manufacture, as used herein, is intended to encompass a computer program accessible from any computer-readable device, carrier, or media.

An indirect calorimetry methodology 400 defines/generates a calorimetry model by regression analysis (block 402). With the model available, individual users can estimate their caloric intake based upon weight and data representative of their amount of exercise. To that end, metrics are tracked that are associated with exercise intensity and duration (block 404). To receive a higher fidelity estimate, user specific demographics are received (e.g., sex, age, height, BMI, etc.) in block 406. A baseline user resting metabolic rate and exercising metabolic rate for their particular demographic group can be used as a starting point (block 408). In some applications, fine tuning of these baselines, depicted at block 410, can be achieved by an initial more rigorous effort, depicted as a calorie journal 412 or by a more clinically accurate technique, depicted as clinically obtained health data 414 or an indirect calorimetric test, depicted as respiration flow/$CO_2$ at 416. Over a period of time (e.g., a week) in block 418, physiological data is tracked. Examples of such data include body temperature (block 420), running mileage (block 422), elevated heart rate for a period of time (block 424), and exercise machine usage data (block 426). This data can be used to calculate calories expended during exercise (block 428). As the conclusion of the tracking period, weight measurement information is received (block 430). This information can be manually input as depicted at 432 or electronically communicated as depicted at 434. Total caloric intake can then be estimated in block 436 based upon these inputs with use of the model. Then, the data and calculations can be reported in block 438.

It should be appreciated with the benefit of the present disclosure that the determination of exercise can benefit from the synergistic combination of sensing multiple parameters associated with physical exercise. For example, a physiological measure of elevated pulse rate can be correlated with a motion detector to determine whether the elevated pulse is an emotional response or due to slow speed exercise such as running or a faster mode such as cycling. A pedometer input can gauge running exertion that can then be correlated with heart rate to gauge how strenuously the user is running or walking.

Figure 5:
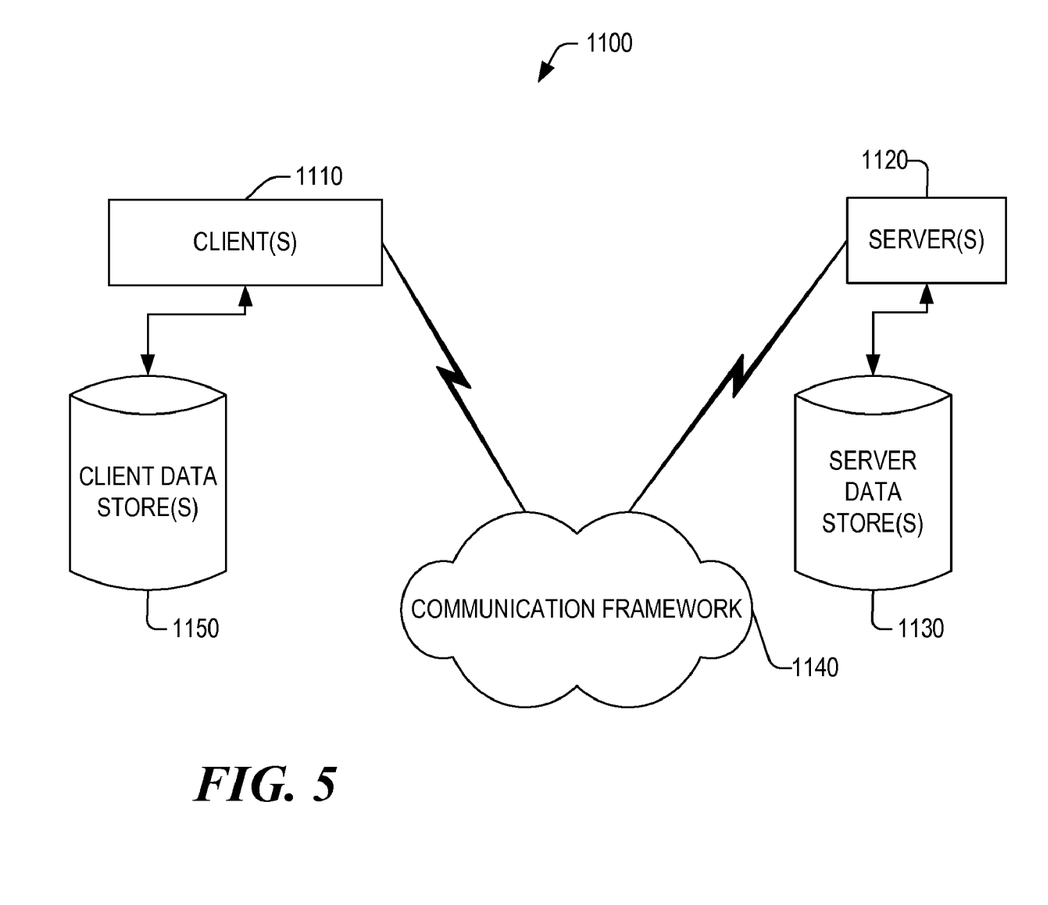
FIG. 5 illustrates an exemplary networking environment, wherein the novel aspects of the claimed subject matter can be employed.
Figure 6:
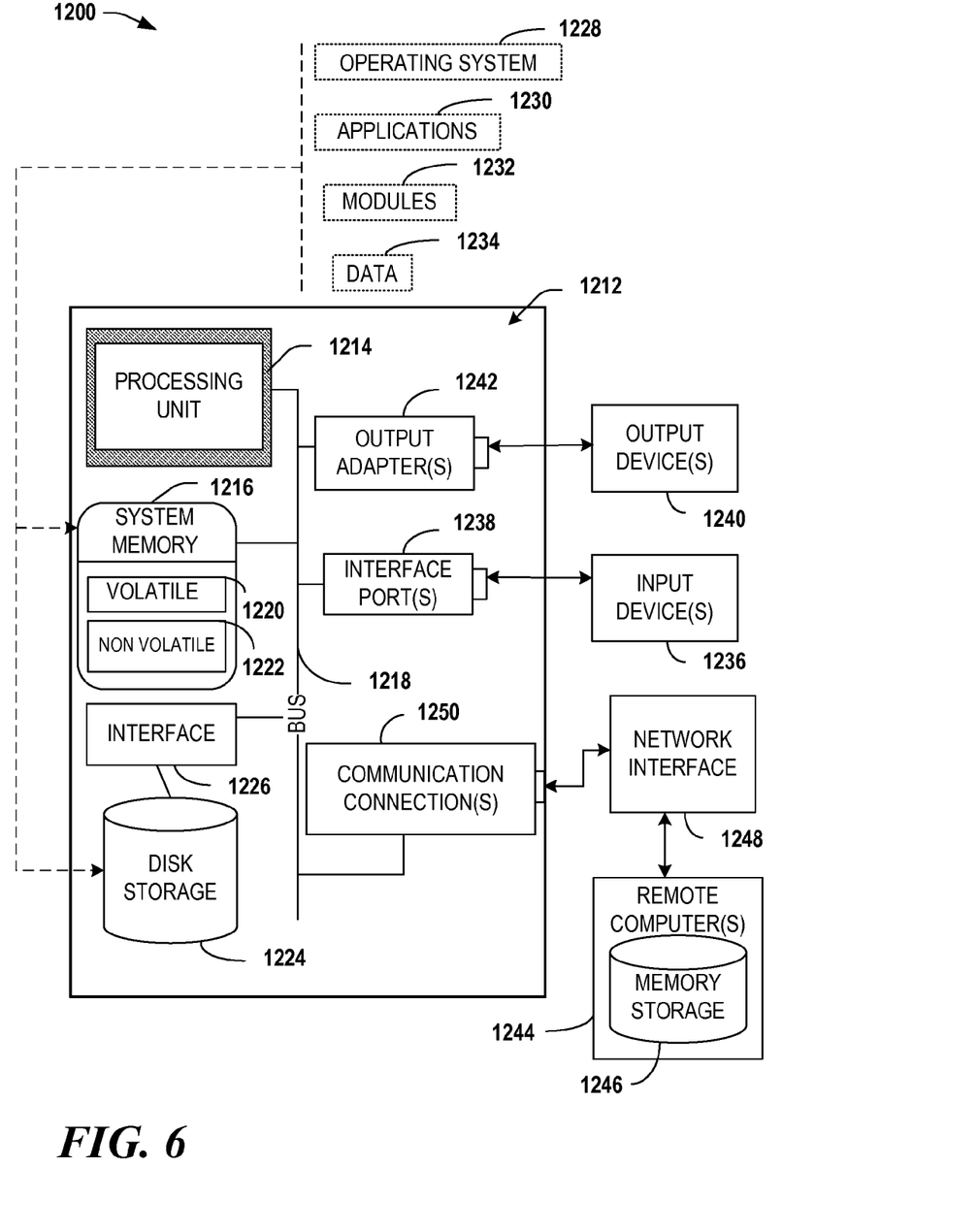
FIG. 6 illustrates an exemplary operating environment that can be employed in accordance with the claimed subject matter.

In order to provide additional context for implementing various aspects of the claimed subject matter, FIGS. 5-6 and the following discussion is intended to provide a brief, general description of a suitable computing environment in which the various aspects of the subject innovation may be implemented. For example, a counselor component that facilitates automatically generating questions to ask a doctor during an appointment, as described in the previous figures, can be implemented in such suitable computing environment. While the claimed subject matter has been described above in the general context of computer-executable instructions of a computer program that runs on a local computer and/or remote computer, those skilled in the art will recognize that the subject innovation also may be implemented in combination with other program modules. Generally, program modules include routines, programs, components, data structures, etc., that perform particular tasks and/or implement particular abstract data types.

Moreover, those skilled in the art will appreciate that the inventive methods may be practiced with other computer system configurations, including single-processor or multi-processor computer systems, minicomputers, mainframe computers, as well as personal computers, hand-held computing devices, microprocessor-based and/or programmable consumer electronics, and the like, each of which may operatively communicate with one or more associated devices. The illustrated aspects of the claimed subject matter may also be practiced in distributed computing environments where certain tasks are performed by remote processing devices that are linked through a communications network. However, some, if not all, aspects of the subject innovation may be practiced on stand-alone computers. In a distributed computing environment, program modules may be located in local and/or remote memory storage devices.

FIG. 5 is a schematic block diagram of a sample-computing environment 1100 with which the claimed subject matter can interact. The system 1100 includes one or more client(s) 1110. The client(s) 1110 can be hardware and/or software (e.g., threads, processes, computing devices). The system 1100 also includes one or more server(s) 1120. The server(s) 1120 can be hardware and/or software (e.g., threads, processes, computing devices). The servers 1120 can house threads to perform transformations by employing the subject innovation, for example.

One possible communication between a client 1110 and a server 1120 can be in the form of a data packet adapted to be transmitted between two or more computer processes. The system 1100 includes a communication framework 1140 that can be employed to facilitate communications between the client(s) 1110 and the server(s) 1120. The client(s) 1110 are operably connected to one or more client data store(s) 1150 that can be employed to store information local to the client(s) 1110. Similarly, the server(s) 1120 are operably connected to one or more server data store(s) 1130 that can be employed to store information local to the servers 1120.

With reference to FIG. 6, an exemplary environment 1200 for implementing various aspects of the claimed subject matter includes a computer 1212. The computer 1212 includes a processing unit 1214, a system memory 1216, and a system bus 1218. The system bus 1218 couples system components including, but not limited to, the system memory 1216 to the processing unit 1214. The processing unit 1214 can be any of various available processors. Dual microprocessors and other multiprocessor architectures also can be employed as the processing unit 1214.

The system bus 1218 can be any of several types of bus structure(s) including the memory bus or memory controller, a peripheral bus or external bus, and/or a local bus using any variety of available bus architectures including, but not limited to, Industrial Standard Architecture (ISA), Micro-Channel Architecture (MSA), Extended ISA (EISA), Intelligent Drive Electronics (IDE), VESA Local Bus (VLB), Peripheral Component Interconnect (PCI), Card Bus, Universal Serial Bus (USB), Advanced Graphics Port (AGP), Personal Computer Memory Card International Association bus (PCM-CIA), Firewire (IEEE 1394), and Small Computer Systems Interface (SCSI).

The system memory 1216 includes volatile memory 1220 and nonvolatile memory 1222. The basic input/output system (BIOS), containing the basic routines to transfer information between elements within the computer 1212, such as during start-up, is stored in nonvolatile memory 1222. By way of illustration, and not limitation, nonvolatile memory 1222 can include read only memory (ROM), programmable ROM (PROM), electrically programmable ROM (EPROM), electrically erasable programmable ROM (EEPROM), or flash memory. Volatile memory 1220 includes random access memory (RAM), which acts as external cache memory. By way of illustration and not limitation, RAM is available in many forms such as static RAM (SRAM), dynamic RAM (DRAM), synchronous DRAM (SDRAM), double data rate SDRAM (DDR SDRAM), enhanced SDRAM (ESDRAM), Synchlink DRAM (SLDRAM), Rambus direct RAM (RDRAM), direct Rambus dynamic RAM (DRDRAM), and Rambus dynamic RAM (RDRAM).

Computer 1212 also includes removable/non-removable, volatile/non-volatile computer storage media. FIG. 6 illustrates, for example, disk storage 1224. Disk storage 1224 includes, but is not limited to, devices like a magnetic disk drive, floppy disk drive, tape drive, Jaz drive, Zip drive, LS-100 drive, flash memory card, or memory stick. In addition, disk storage 1224 can include storage media separately or in combination with other storage media including, but not limited to, an optical disk drive such as a compact disk ROM device (CD-ROM), CD recordable drive (CD-R Drive), CD rewritable drive (CD-RW Drive) or a digital versatile disk ROM drive (DVD-ROM). To facilitate connection of the disk storage devices 1224 to the system bus 1218, a removable or non-removable interface is typically used such as interface 1226.

It is to be appreciated that FIG. 6 describes software that acts as an intermediary between users and the basic computer resources described in the suitable operating environment 1200. Such software includes an operating system 1228. Operating system 1228, which can be stored on disk storage 1224, acts to control and allocate resources of the computer system 1212. System applications 1230 take advantage of the management of resources by operating system 1228 through program modules 1232 and program data 1234 stored either in system memory 1216 or on disk storage 1224. It is to be appreciated that the claimed subject matter can be implemented with various operating systems or combinations of operating systems.

A user enters commands or information into the computer 1212 through input device(s) 1236. Input devices 1236 include, but are not limited to, a pointing device such as a mouse, trackball, stylus, touch pad, keyboard, microphone, joystick, game pad, satellite dish, scanner, TV tuner card, digital camera, digital video camera, web camera, and the like. These and other input devices connect to the processing unit 1214 through the system bus 1218 via interface port(s) 1238. Interface port(s) 1238 include, for example, a serial port, a parallel port, a game port, and a universal serial bus (USB). Output device(s) 1240 use some of the same type of ports as input device(s) 1236. Thus, for example, a USB port may be used to provide input to computer 1212 and to output information from computer 1212 to an output device 1240. Output adapter 1242 is provided to illustrate that there are some output devices 1240 like monitors, speakers, and printers, among other output devices 1240, which require special adapters. The output adapters 1242 include, by way of illustration and not limitation, video and sound cards that provide a means of connection between the output device 1240 and the system bus 1218. It should be noted that other devices and/or systems of devices provide both input and output capabilities such as remote computer(s) 1244.

Computer 1212 can operate in a networked environment using logical connections to one or more remote computers, such as remote computer(s) 1244. The remote computer(s) 1244 can be a personal computer, a server, a router, a network PC, a workstation, a microprocessor based appliance, a peer device or other common network node and the like, and typically includes many or all of the elements described relative to computer 1212. For purposes of brevity, only a memory storage device 1246 is illustrated with remote computer(s) 1244. Remote computer(s) 1244 is logically connected to computer 1212 through a network interface 1248 and then physically connected via communication connection 1250. Network interface 1248 encompasses wire and/or wireless communication networks such as local-area networks (LAN) and wide-area networks (WAN). LAN technologies include Fiber Distributed Data Interface (FDDI), Copper Distributed Data Interface (CDDI), Ethernet, Token Ring and the like. WAN technologies include, but are not limited to, point-to-point links, circuit switching networks like Integrated Services Digital Networks (ISDN) and variations thereon, packet switching networks, and Digital Subscriber Lines (DSL).

Communication connection(s) 1250 refers to the hardware/software employed to connect the network interface 1248 to the bus 1218. While communication connection 1250 is shown for illustrative clarity inside computer 1212, it can also be external to computer 1212. The hardware/software necessary for connection to the network interface 1248 includes, for exemplary purposes only, internal and external technologies such as, modems including regular telephone grade modems, cable modems and DSL modems, ISDN adapters, and Ethernet cards.

What has been described above includes examples of the subject innovation. It is, of course, not possible to describe every conceivable combination of components or methodologies for purposes of describing the claimed subject matter, but one of ordinary skill in the art may recognize that many further combinations and permutations of the subject innovation are possible. Accordingly, the claimed subject matter is intended to embrace all such alterations, modifications, and variations that fall within the spirit and scope of the appended claims.

In particular and in regard to the various functions performed by the above described components, devices, circuits, systems and the like, the terms (including a reference to a "means") used to describe such components are intended to correspond, unless otherwise indicated, to any component which performs the specified function of the described component (e.g., a functional equivalent), even though not structurally equivalent to the disclosed structure, which performs the function in the herein illustrated exemplary aspects of the claimed subject matter. In this regard, it will also be recognized that the innovation includes a system as well as a computer-readable medium having computer-executable instructions for performing the acts and/or events of the various methods of the claimed subject matter.

There are multiple ways of implementing the present innovation, e.g., an appropriate API, tool kit, driver code, operating system, control, standalone or downloadable software object, etc. which enables applications and services to use the advertising techniques of the invention. The claimed subject matter contemplates the use from the standpoint of an API (or other software object), as well as from a software or hardware object that operates according to the advertising techniques in accordance with the invention. Thus, various implementations of the innovation described herein may have aspects that are wholly in hardware, partly in hardware and partly in software, as well as in software.

The aforementioned systems have been described with respect to interaction between several components. It can be appreciated that such systems and components can include those components or specified sub-components, some of the specified components or sub-components, and/or additional components, and according to various permutations and combinations of the foregoing. Sub-components can also be implemented as components communicatively coupled to other components rather than included within parent components (hierarchical). Additionally, it should be noted that one or more components may be combined into a single component providing aggregate functionality or divided into several separate sub-components, and any one or more middle layers, such as a management layer, may be provided to communicatively couple to such sub-components in order to provide integrated functionality. Any components described herein may also interact with one or more other components not specifically described herein but generally known by those of skill in the art.

In addition, while a particular feature of the subject innovation may have been disclosed with respect to only one of several implementations, such feature may be combined with one or more other features of the other implementations as may be desired and advantageous for any given or particular application. Furthermore, to the extent that the terms "includes," "including," "has," "contains," variants thereof, and other similar words are used in either the detailed description or the claims, these terms are intended to be inclusive in a manner similar to the term "comprising" as an open transition word without precluding any additional or other elements.

What is claimed is:

1. A processor-executable method for determining nutritional caloric intake, comprising:
    detecting, from a portable sensor adapted to be worn by a user, a parameter associated with physical exercise over a measurement period;
    comparing a current weight measurement of the user with a stored prior weight measurement at the beginning of the measurement period;
    accessing a model for caloric intake stored in memory, the model for caloric intake being trained by regression analysis based upon caloric intake and weight changes monitored for a population of a plurality of individuals; and
    estimating, by one or more processors, total caloric intake consumed by the user based upon the detected parameter, the prior weight, the current weight, and the caloric intake model.

2. The method of claim 1, further comprising:
    periodically weighing the population; and
    training the caloric intake model by regression analysis based upon the monitored caloric intake and population weights.

3. The method of claim 1, further comprising:
    receiving a demographic classification for a user; and
    accessing the model for caloric intake based upon the demographic classification.

4. The method of claim 1, further comprising detecting a parameter associated with body motion to determine physical exercise.

5. The method of claim 4, further comprising detecting a parameter associated with a selected one from a group consisting of global positioning satellites signals, pedometer signal, and an accelerometer signal.

6. The method of claim 1, further comprising detecting a parameter associated with physiological exertion to determine physical exercise.

7. The method of claim 6, further comprising detecting a parameter selected from a group consisting of elevated pulse, skin resistance, skin temperature, heart rate, and respiration rate.

8. The method of claim 1, further comprising detecting a parameter received from an exercise machine.

9. The method of claim 1, further comprising fine tuning a metabolic baseline for the user by receiving tracking data for caloric intake during an initial period for accessing the caloric intake model.

10. The method of claim 9, further comprising calculating caloric intake from a calorie journal.

11. The method of claim 1, further comprising receiving a weight measurement periodically from an electronically communicating scale.

12. A processor-executable method for determining nutritional caloric intake, comprising:
    detecting, from a first portable sensor adapted to be worn by a user, a physiological parameter associated with physical exercise over a measurement period;
    detecting, from a second portable sensor adapted to be worn by the user, a motion parameter associated with physical exercise over the measurement period;
    comparing a current weight measurement of the user with a stored prior weight measurement at the beginning of the measurement period;

accessing a model for caloric intake trained by performing regression analysis on caloric intake, weight changes, physiological sensing data, and exercise monitor data for a control population of a plurality of individuals, the model for caloric intake stored in memory; and estimating, by one or more processors, total caloric intake consumed by the user based upon the detected physiological and motion parameters and the caloric intake model.

13. The processor-executable method of claim 1, further comprising:
differentiating the population based on a plurality of demographic profiles; and
training the caloric intake model by regression analysis based upon the plurality of demographic profiles.

14. The processor-executable method of claim 13, wherein the plurality of demographic profiles include at least one of gender, age, height, and body mass index.

15. The processor-executable method of claim 12, wherein the model for caloric intake is trained by performing regression analysis on a plurality of demographic profiles for the control population.

16. The processor-executable method of claim 12, further comprising automatically generating one or more questions to ask to a doctor in response to the estimating of the total caloric intake.

17. A system comprising:
a processor; and
a memory communicatively coupled to the processor that stores computer-readable instructions that, when executed by the processor, perform operations comprising:
detecting a parameter associated with physical exercise over a measurement period, the parameters including physiological and motion parameters;
comparing a current weight measurement of the user with a stored prior weight measurement at the beginning of the measurement period;
accessing a model for caloric intake stored in memory, the model for caloric intake being trained by regression analysis based upon caloric intake and weight changes monitored for a control population of a plurality of individuals; and
estimating total caloric intake consumed by the user based upon the detected physiological and motion parameters, the prior weight, the current weight, and the caloric intake model.

18. The system of claim 17, wherein the operations further comprise:
receive additional weight measurements of the user to be used with the model for caloric intake to determine excess or deficit calories corresponding to a change in weight.

19. The system of claim 17, wherein the operations further comprise:
differentiate the population based on a plurality of demographic profiles; and
train the caloric intake model by regression analysis based upon the plurality of demographic profiles.

20. The system of claim 19, wherein the plurality of demographic profiles include at least one of gender, age, height, and body mass index.

* * * * *